United States Patent
Minami et al.

(10) Patent No.: US 12,059,442 B2
(45) Date of Patent: Aug. 13, 2024

(54) OBESITY TREATMENT USING PROBIOTICS, COMPOSITION FOR REDUCING BODY FAT, AND COMPOSITION FOR REDUCING WAIST CIRCUMFERENCE

(71) Applicant: MORINAGA MILK INDUSTRY CO., LTD., Tokyo (JP)

(72) Inventors: Junichi Minami, Kanagawa (JP); Akira Sen, Kanagawa (JP)

(73) Assignee: MORINAGA MILK INDUSTRY CO., LTD., Tokyo (JP)

( * ) Notice: Subject to any disclaimer, the term of this patent is extended or adjusted under 35 U.S.C. 154(b) by 0 days.

(21) Appl. No.: 16/981,417

(22) PCT Filed: Mar. 27, 2019

(86) PCT No.: PCT/JP2019/013272
§ 371 (c)(1),
(2) Date: Mar. 11, 2021

(87) PCT Pub. No.: WO2019/189408
PCT Pub. Date: Oct. 3, 2019

(65) Prior Publication Data
US 2021/0196767 A1    Jul. 1, 2021

(30) Foreign Application Priority Data
Mar. 29, 2018   (JP) .................. 2018-064982

(51) Int. Cl.
*A61K 35/745* (2015.01)
*A61K 35/00* (2006.01)
*A61K 35/747* (2015.01)

(52) U.S. Cl.
CPC .......... *A61K 35/745* (2013.01); *A61K 35/747* (2013.01); *A61K 2035/115* (2013.01)

(58) Field of Classification Search
None
See application file for complete search history.

(56) References Cited

U.S. PATENT DOCUMENTS

| | | | |
|---|---|---|---|
| 8,497,114 B2 * | 7/2013 | Kondo ................... | C12N 1/205 424/93.4 |
| 10,405,563 B2 * | 9/2019 | Li ......................... | A23K 20/158 |
| 2012/0171167 A1 * | 7/2012 | Kondo ..................... | A61P 3/08 424/93.4 |

FOREIGN PATENT DOCUMENTS

| CN | 102970997 A | 3/2013 |
|---|---|---|
| CN | 107684567 A | 2/2018 |
| CN | 107760620 A | 3/2018 |
| JP | 2015-127340 A | 7/2015 |
| WO | WO2011/034166 A1 | 3/2011 |

OTHER PUBLICATIONS

Ji et al. "Modulation of the murine microbiome with a concomitant anti-obesity effect by Lactobacillus rhamnosus GG and Lactobacillus sakei NR2". Beneficial Microbes, Mar. 2012, 3 (1), pp. 13-22.*
Turnbaugh et al. "An obesity-associated gut microbiome with increased capacity for energy harvest". Nature, 2006, vol. 44, (21/28), pp. 1027-1031.*
Rosenbaum, M., et al., "The gut microbiota in human energy homeostasis and obesity," Trends Endocrinol. Metab. 2015;26(9):493-501.
Backhed, F., et al., "The gut microbiota as an environmental factor that regulates fat storage," PNAS 2004;101(44):15718-15723.
Tremaroli, V., et al., "Functional interactions between the gut microbiota and host metabolism," Nature 2012;489:242-249.
Borgeraas, H., et al., "Effects of probiotics on body weight, body mass index, fat mass and fat percentage in subjects with overweight or obesity: a systematic review and meta-analysis of randomized controlled trials," Obesity Rev. 2018;19:219-232.
Salonen, A., et al., "Impact of diet and individual variation on intestinal microbiota composition and fermentation products in obese men," The Isme Journal 2014;8:2218-2230.
Kadooka, Y., et al., "Special Featue: Health Effects of Lactic Acid Bacteria—From the Latest Research Results. An Effect of Lactobacillus gasseri on Inhibition of Visceral Fat Accumulation," Food Industry 2012;55(4):54-58, with English language translation thereof.
Ley, R., et al., "Human gut microbes associated with obesity," Nature 2006;444:1022-1023.
Yildiran, H., et al., "Does intestinal microbiota affect body weight?" Obesity Facts 2016;9(suppl. 1):204.
International Search Report for PCT Patent App. No. PCT/JP2019/013272 (Jun. 11, 2019).
Office Action from Taiwanese Patent App. No. 108111102 issued on Sep. 7, 2022, with English language translation thereof.
Office Action from Japanese Patent App. No. 2020-509216 issued on Feb. 14, 2023, with English language translation thereof.
Food Industry, vol. 55; pp. 54-58, 2012; with English Abstract.
Verdam, F., et al; "Human Intestinal Microbiota Composition Is Associated with Local and Systemic Inflammation in Obesity", Obesity, vol. 21; No. 12, Dec. 2013; pp E607-E615A.
Compare, D., et al.; "The Gut Bacteria-Driven Obesity Development"; Digestive Diseases, vol. 34, pp. 221-229, 2016.
Decision of Refusal issued by the Taiwan Intellectual Property Office on Aug. 18, 2023 for Application No. 108111102, with English language translation thereof.

* cited by examiner

*Primary Examiner* — Vera Afremova
(74) *Attorney, Agent, or Firm* — Cermak & McGowan LLP; Shelly Guest Cermak

(57) ABSTRACT

Provided are means, methods, and compositions effective for obesity treatment using probiotics such as bifidobacteria or lactobacilli. Also, a method of selecting probiotic bacteria having a body fat reducing effect, and a method of selecting responders to probiotic bacteria having an anti-obesity action are provided. Provided is a composition for reducing body fat, or the like, which contains *Bifidobacterium* and/or lactobacilli as an active ingredient, and is used for a pre-obesity group or an obesity disease including intestinal flora in which the ratio of the phylum Firmicutes to the phylum Bacteroidetes has a high value.

1 Claim, 1 Drawing Sheet

Specification includes a Sequence Listing.

OBESITY TREATMENT USING PROBIOTICS, COMPOSITION FOR REDUCING BODY FAT, AND COMPOSITION FOR REDUCING WAIST CIRCUMFERENCE

This application is a national phase entry under 35 U.S.C. § 371 of PCT Patent Application No. PCT/JP2019/013272, filed on Mar. 27, 2019, which claims priority under 35 U.S.C. § 119 to Japanese Patent Application No. 2018-064982, filed Mar. 29, 2018, both of which are incorporated by reference. Also, the Sequence Listing filed electronically herewith is hereby incorporated by reference (File name: 2020-09-16T_216-034_Seq List; File size: 2 KB; Date recorded: Sep. 16, 2020).

TECHNICAL FIELD

The present technology relates to obesity treatment using probiotics, a composition for reducing body fat, and a composition for reducing waist circumference, and more specifically relates to means, methods, and compositions that are effective in obesity treatment using probiotics such as bifidobacteria or lactobacilli.

BACKGROUND ART

Obesity is defined as a physical situation in which obesity tissues are accumulated above normal levels. Becoming obese causes various diseases such as hypertension, cardiovascular disorders, hyperlipidaemia, arteriosclerosis, and diabetes, and complications such as vascular disorders, visual impairment, neuropathy, and resistance reduction also occur. The cause of the obesity is mainly that energy intake is more than consumed energy, and it has also been reported that intestinal flora is related to energy acquisition or homeostasis, and fat tissue accumulation (Non-Patent Literatures 1 to 3).

Therefore, in recent years, regarding the relationship between intestinal flora and obesity, the need for clarification is increasing. Non-Patent Literature 4 reports the result of meta-analysis of an intervention test using probiotics, as an effort to improve obesity by targeting intestinal flora, which suggests that there is a possibly that ingestion of probiotics may significantly reduce body weight, also called BMI, and body fat percentage as compared to placebo but also discloses that the effect is small. Also, Non-Patent Literature 5 suggests that there are responders and non-responders according to the diversities of intestinal flora in subjects in an obesity improvement test by ingestion of three types of dietary fiber. However, until now, no knowledge or report has been made regarding what kind of subject can be targeted in the obesity improvement test by ingestion of probiotics.

CITATION LIST

Non-Patent Literature

Non-Patent Literature 1: M. Rosenbaum, R. Knight, and R. L. Leibel, "The gut microbiota in human energy homeostasis and obesity.," Trends Endocrinol. Metab., vol. 26, no. 9, pp. 493-501, September 2015.
Non-Patent Literature 2: F. Backhed et al., "The gut microbiota as an environmental factor that regulates fat storage.," Proc. Natl. Acad. Sci. U.S.A, vol. 101, no. 44, pp. 15718-23, November 2004.
Non-Patent Literature 3: V. Tremaroli and F. Backhed, "Functional interactions between the gut microbiota and host metabolism.," Nature, vol. 489, no. 7415, pp. 242-9, September 2012.
Non-Patent Literature 4: H. Borgeraas et al., "Effects of probiotics on body weight, body mass index, fat mass and fat percentage in subjects with overweight or obesity: a systematic review and meta-analysis of randomized controlled trials." Obes Rev. 19(2):219-232, February 2018.
Non-Patent Literature 5: Salonen A, Lahti L, Salojarvi J, et al. Impact of diet and individual variation on intestinal microbiota composition and fermentation products in obese men. ISME J. 2014; 8(11):2218-2230. doi:10.1038/ismej.2014.63.

SUMMARY OF INVENTION

Technical Problem

As described above, although the relationship between intestinal flora and obesity has already been reported, the effect of obesity treatment by ingestion of probiotics is small. Thus, there are circumstances that further studies are desired in order to find a more effective treatment method for obesity.

Therefore, a main aspect of the present technology is to provide means, methods, and compositions effective in obesity treatment using probiotics such as Bifidobacteria or lactobacilli. Also, the main aspect is to provide a method of selecting probiotic bacteria having a body fat reducing effect, and a method of selecting responders to probiotic bacteria having an anti-obesity action.

Means to Solve the Problem

That is, first, the present technology provides a composition for reducing body fat, which contains *Bifidobacterium* and/or lactobacilli as an active ingredient, and is administered to for a pre-obese group of subjects or an obese group of subjects, all having intestinal flora in which a ratio of the phylum Firmicutes to the phylum Bacteroidetes has a high value.

In the composition for reducing body fat according to the present technology, the ratio of the phylum Firmicutes to the phylum Bacteroidetes may be 1.3 or more.

Also, in the composition for reducing body fat according to the present technology, the *Bifidobacterium* may be any one or more types of a group including *Bifidobacterium longum* subspecies *longum*, *Bifidobacterium bifidum*, *Bifidobacterium breve*, *Bifidobacterium longum* subspecies *infantis*, *Bifidobacterium adolescentis*, *Bifidobacterium catenulatum*, *Bifidobacterium pseudocatenulatum*, *Bifidobacterium animalis* subspecies *animalis*, and *Bifidobacterium animalis* subspecies *lactis*. In this case, the *Bifidobacterium breve* may be *Bifidobacterium breve* MCC1274 (FERM BP-11175).

Also, in the composition for reducing body fat according to the present technology, the lactobacilli may be any one or more types of a group including *Lactobacillus plantarum*, *Lactobacillus casei*, *Lactobacillus acidophilus*, *Lactobacillus delbrueckii* subspecies *bulgaricus*, *Lactobacillus gasseri*, *Lactobacillus amylovora*, *Lactobacillus reuteri*, *Lactobacillus rhamnosus*, *Lactobacillus paracasei*, *Lactobacillus fermentum*, *Lactobacillus salivarius*, and *Lactobacillus lactis*.

Also, the present technology provides a method including at least (1) classifying subjects into groups (a) and (b), wherein said group (a) subjects have a high value ratio of the phylum Firmicutes to the phylum Bacteroidetes, and wherein said group (b) subjects are all those not belonging to the group (a), wherein said classifying is by measuring composition ratios of intestinal flora of a target at a phylum level;

(2) administering probiotic bacteria to subjects in each of the groups (a) and (b) classified in the step (1); and (3) measuring body fat of subjects in each group (a) and (b), (4) selecting probiotic bacteria having an anti-obesity action on the subjects of group (a) or (b).

Also, the present technology provides a method of selecting responders to probiotic bacteria having an anti-obesity action at least through:

(1) administering probiotic bacteria having the anti-obesity action to more than one subject; and (2) classifying the more than one subject into groups (c) and (d), wherein group (c) subjects have a high value ratio of the phylum Firmicutes to the phylum Bacteroidetes, and wherein said group (d) subjects are all those not belonging to the group (c), wherein said classifying is by measuring composition ratios of intestinal flora of the subject at a phylum level.

In the present technology, in the subjects of group, the high value ratio of the phylum Firmicutes to the phylum Bacteroidetes may be 1.3 or more.

Also, in the present technology, the probiotic bacteria may be *Bifidobacterium* and/or lactobacilli.

Also, in the present technology, the *Bifidobacterium* may be any one or more types of a group including *Bifidobacterium longum* subspecies *longum*, *Bifidobacterium bifidum*, *Bifidobacterium breve*, *Bifidobacterium longum* subspecies *infantis*, *Bifidobacterium adolescentis*, *Bifidobacterium catenulatum*, *Bifidobacterium pseudocatenulatum*, *Bifidobacterium animalis* subspecies *animalis*, and *Bifidobacterium animalis* subspecies *lactis*. In this case, the *Bifidobacterium breve* may be *Bifidobacterium breve* MCC1274 (FERN BP-11175).

Besides, in the present technology, the lactobacilli may be any one or more types of a group including *Lactobacillus plantarum*, *Lactobacillus casei*, *Lactobacillus acidophilus*, *Lactobacillus delbrueckii* subspecies *bulgaricus*, *Lactobacillus gasseri*, *Lactobacillus amylovora Lactobacillus reuteri*, *Lactobacillus rhamnosus*, *Lactobacillus paracasei*, *Lactobacillus fermentum*, *Lactobacillus salivarius*, and *Lactobacillus lactis*.

Also, the present technology provides a composition for reducing waist circumference, which contains *Bifidobacterium* and/or lactobacilli as an active ingredient, and is administered to a pre-obese group of subjects or an obese group of subjects.

The composition for reducing waist circumference according to the present technology may be administered to the pre-obese group of subjects or the obese group of subjects, all of whom have a high value ratio of the phylum Firmicutes to the phylum Bacteroidetes.

Also, in the composition for reducing waist circumference according to the present technology, the *Bifidobacterium* may be any one or more types of a group including *Bifidobacterium longum* subspecies *longum*, *Bifidobacterium bifidum*, *Bifidobacterium breve*, *Bifidobacterium longum* subspecies *infantis*, *Bifidobacterium adolescentis*, *Bifidobacterium catenulatum*, *Bifidobacterium pseudocatenulatum*, *Bifidobacterium animalis* subspecies *animalis*, and *Bifidobacterium animalis* subspecies *lactis*. In this case, the *Bifidobacterium breve* may be *Bifidobacterium breve* MCC1274 (FERN BP-11175).

Also, in the composition for reducing waist circumference according to the present technology, the lactobacilli may be any one or more types of a group including *Lactobacillus plantarum*, *Lactobacillus casei*, *Lactobacillus acidophilus*, *Lactobacillus delbrueckii* subspecies *bulgaricus*, *Lactobacillus gasseri*, *Lactobacillus amylovora*, *Lactobacillus reuteri*, *Lactobacillus rhamnosus*, *Lactobacillus paracasei*, *Lactobacillus fermentum*, *Lactobacillus salivarius*, and *Lactobacillus lactis*.

In the present technology, a "pre-obese group" refers to subjects with mild obesity defined as a BMI (Body Mass Index) value of 25 or more and less than 30, and subjects with "obesity disease" refers to obesity defined as a BMI value of 30 or more. Also, "probiotic bacteria" refer to bacteria that perform a beneficial action in the intestine. Also, "responders" refer to people whose obesity indices such as a body weight, body fat, and visceral fat are improved by ingestion of an anti-obesity composition, as compared to those before ingestion or in the control, or a group whose obesity indices are remarkably improved as compared to those in the overall analysis, in a clinical test, etc.

Advantageous Effects of Invention

According to the present technology, it is possible to provide obesity treatment using probiotics, a composition for reducing body fat and a composition for reducing waist circumference.

The effect of the present technology is not necessarily limited to the effect described herein, and may be any of effects described in this disclosure.

DESCRIPTION OF EMBODIMENTS

Figure 1:
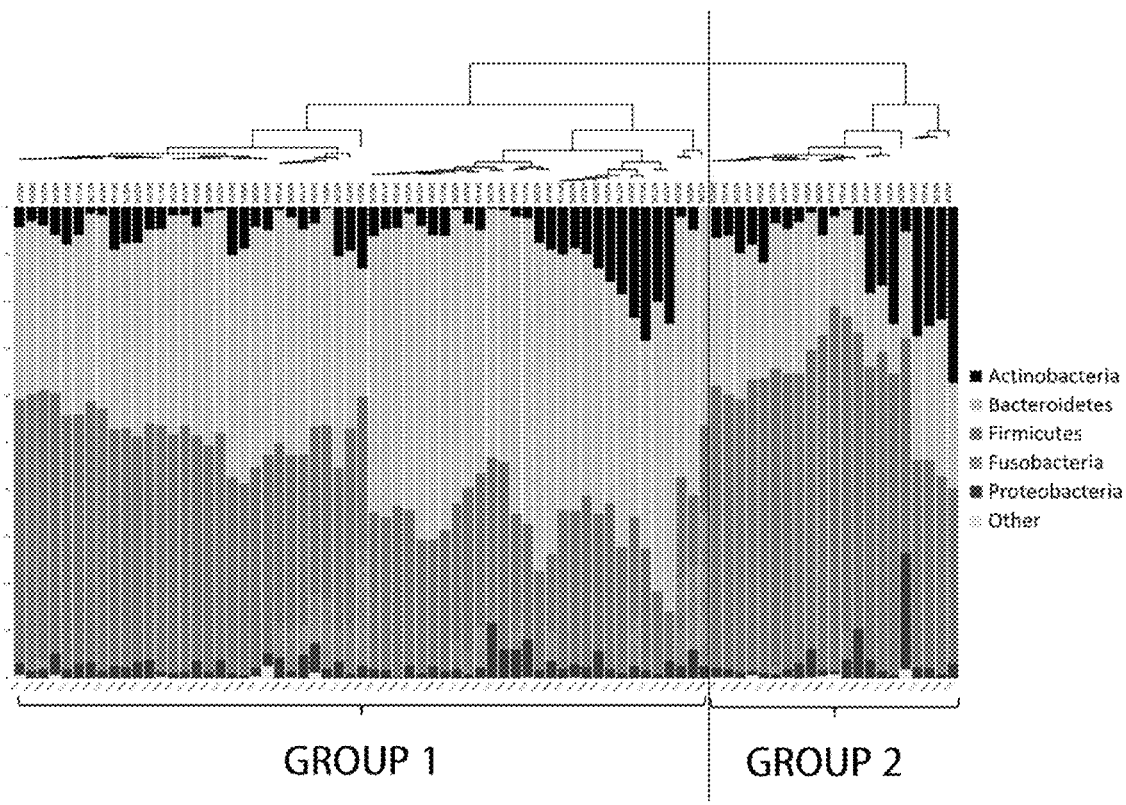
FIG. 1 illustrates the result of classifying two groups of subjects obtained by hierarchically clustering subjects on the basis of the degree of similarity of composition ratios of intestinal bacteria before test start (0th week), and the intestinal bacteria composition of each subject at the phylum level.

Hereinafter, a suitable mode for carrying out the present technology will be described.

The embodiment described below is described as a representative embodiment of the present technology, by which the scope of the present technology is not narrowly construed.

<1. Composition>

A composition for reducing body fat according to the present technology is characterized in that it contains *Bifidobacterium* and/or lactobacilli as an active ingredient, and is used for a pre-obese group of subjects or an obese group of subjects, wherein the subjects have intestinal flora in which the ratio of the phylum Firmicutes to the phylum Bacteroidetes has a high value. Also, a composition for reducing waist circumference according to the present technology is characterized in that it contains *Bifidobacterium* and/or lactobacilli as an active ingredient, and is used for a pre-obese group of subjects or an obese group of subjects.

(1) *Bifidobacterium*

Examples of *Bifidobacterium* (also called "bifidobacteria") may include *Bifidobacterium longum* subspecies *longum*, *Bifidobacterium bifidum*, *Bifidobacterium breve*, *Bifidobacterium longum* subspecies *infantis*, *Bifidobacterium adolescentis*, *Bifidobacterium catenulatum*, *Bifidobacterium pseudocatenulatum*, *Bifidobacterium animalis* subspecies *animalis*, *Bifidobacterium animalis* subspecies *lactis*, and the like. In the present technology, it is desirable to use these as for the *Bifidobacterium*, and from these, one type may be used alone, or any combination of two or more types may be used. In this specification, the expression "bacteria" also includes the concept of "strain."

In the present technology, among these, it is particularly desirable to use *Bifidobacterium breve*.

Examples of *Bifidobacterium breve* may include *Bifidobacterium breve* MCC1274 (FERM BP-11175), *Bifidobacterium breve* M-16V (NITE BP-02622), UCC2003, YIT4010, YIT4064, BBG-001, BR-03, B632 (DSMZ 24706), C50, Bb99 (DSM 13692), R0070, ATCC15700, ATCC15698, DSM 24732, and the like, and among these, it is desirable to use *Bifidobacterium breve* MCC1274 (FERN BP-11175) and/or *Bifidobacterium breve* M-16V (NITE BP-02622).

*Bifidobacterium breve* MCC1274 (FERN BP-11175) was deposited and given a deposit number of IPOD FERN BP-11175 at the Patent Organism Depository Center, National Institute of Advanced Industrial Science and Technology (Central 6, 1-1-1 Higashi, Tsukuba, Ibaraki, 305-8566, Japan (at present, IPOD Patent Organism Depository Center, National Institute of Technology and Evaluation (NITE-IPOD): Room No. 120, 2-5-8 Kazusakamatari Kisarazu Chiba 292-0818, Japan)) on Aug. 25, 2009.

*Bifidobacterium·breve* M-16V (NITE BP-02622) was internationally deposited in accordance with the Budapest Treaty and given a deposit number of NITE BP-02622 at Patent Microorganism Depository Center, National Institute of Technology and Evaluation (NPMD): Room No. 122, 2-5-8 Kazusakamatari Kisarazu Chiba 292-0818, Japan, on Jan. 26, 2018.

In the present technology, it is particularly desirable to use *Bifidobacterium breve* MCC1274 (FERN BP-11175) as *Bifidobacterium breve*.

(2) Lactobacilli

Examples of lactobacilli may include *Lactobacillus plantarum*, *Lactobacillus casei*, *Lactobacillus acidophilus*, *Lactobacillus delbrueckii* subspecies *bulgaricus*, *Lactobacillus gasseri*, *Lactobacillus amylovora*, *Lactobacillus reuteri*, *Lactobacillus rhamnosus*, *Lactobacillus paracasei*, *Lactobacillus fermentum*, *Lactobacillus salivarius*, *Lactobacillus lactis*, and the like. In the present technology, it is desirable to use these as for lactobacilli, and among these, one type may be used alone, or any combination of two or more types may be used.

The strain specified by the above-exemplified strain name is not limited to the strain itself that has been deposited or registered in a predetermined institution with the corresponding strain name (hereinafter, for convenience of explanation, also referred to as a "deposited strain"), but also includes a strain substantially equivalent thereto (also referred to as a "derivative strain" or an "induced strain"). That is, for example, "*Bifidobacterium breve* MCC1274 (FERN BP-11175)" is not limited to a strain itself that has been deposited in the depository with a deposit number of MCC1274 (FERM BP-11175), but also includes a strain substantially equivalent thereto.

For a strain, "the strain substantially equivalent to the deposited strain" refers to a strain belonging to the same species as the deposited strain, in which the effect of the present technology, that is, a body fat reducing effect or a waist circumference reducing effect may be obtained. The strain substantially equivalent to the deposited strain may be, for example, a derivative strain whose parent strain is the corresponding deposited strain. The derivative strain may include a strain bred from the deposited strain or a strain naturally occurring from the deposited strain.

Examples of the substantially identical strains and derivative strains may include the following strains:

(i) a strain determined as an identical strain by an RAPD method (Randomly Amplified Polymorphic DNA) or a PFGE method (pulsed-field gel electrophoresis) (described in Probiotics in food/Health and nutritional properties and guidelines for evaluation 85, Page 43)

(ii) a strain that has only the genes derived from the corresponding deposited strain, has no foreign-derived genes, and has a DNA identity of 95% or more (iii) a strain bred from the corresponding strain (including genetic engineering alterations, mutations, and natural mutations), and a strain having the same trait.

(3) Others

For example, *Bifidobacterium* and/or lactobacilli to be used in the present technology may be easily acquired by culturing the above described bacteria. The culturing method is not particularly limited as long as these bacteria can grow, and culturing may be carried out under a proper condition depending on the nature of bacteria. Specifically, for example, the culturing temperature is generally 25 to 50° C., preferably 35 to 42° C. Also, the culturing may be preferably carried out under anaerobic conditions, and the culturing may be carried out while, for example, an anaerobic gas such as a carbon dioxide gas is aerated. Also, the culturing may be carried out under slightly aerobic conditions in liquid static culture. *Bifidobacterium* and/or lactobacilli to be used are preferably live bacteria, but may be dead bacteria. In the case of live bacteria, it is desirable to perform treatment by a bacterial fluid freezing method, a spray drying method, a freeze drying method, or an oil drop method. The dead bacteria may include dead bacteria and the like sterilized by heating, freeze-drying, or the like. Other methods for preparing dead microbial cells may include a spray drying method, a retort sterilization method, a freeze drying method, a UHT sterilization method, a pressure sterilization method, a high pressure steam sterilization method, a dry heat sterilization method, a circulating steam sterilization method, an electromagnetic wave sterilization method, an electron beam sterilization method, a high frequency sterilization method, a radiation sterilization method, an ultraviolet sterilization method, an ethylene oxide gas sterilization method, a hydrogen peroxide gas plasma sterilization method, a chemical sterilization method (an alcohol sterilization method, a formalin fixation method, an electrolyzed water treatment method), and the like.

Also, the present microbial cells may be a crushed product. The crushed product may be one obtained by crushing live bacteria, may be one obtained by crushing dead bacteria, and may be one obtained by performing heating, freeze-drying, or the like after crushing. Also, as crushing, crushing through, for example, physical crushing, enzyme lysis treatment, chemical treatment, self-dissolution treatment, or the like, which uses methods and devices conventionally known in the corresponding technical field, may be selected.

Physical crushing may be made by either treatment in the state of microbial cell suspension or treatment in the state of microbial cell powder. As an example of physical crushing, crushing by stirring using an ultrasonic homogenizer, a homogenizer, a ball mill, a beads mill, a dyno mill, a planetary mill, etc., crushing by pressurization using a jet mill, a French press, a cell crusher, etc. or crushing by damaging microbial cells through filter filtration may be selected.

In the enzyme lysis treatment, for example, an enzyme such as lysozyme may be used to destroy the cell structure of lactobacilli microbial cells.

In the chemical treatment, a surfactant such as soybean phospholipid, or glycerin fatty acid ester may be used to destroy the cell structure of lactobacilli microbial cells.

In the self-dissolution treatment, lactobacilli microbial cells may be dissolved by enzymes of some lactobacilli themselves.

In the present technology, physical crushing is preferred because there is no need to add other chemicals or compounds.

A culture medium for culturing *Bifidobacterium* and/or lactobacilli to be used in the present technology is not particularly limited, and a culture medium generally used for culturing the *Bifidobacterium* and/or the lactobacilli may be used.

That is, as for carbon sources, for example, saccharides such as glucose, galactose, lactose, arabinose, mannose, sucrose, starch, starch hydrolysate, blackstrap molasses, glucomannan, and gluco oligosaccharide may be used depending on the assimilability. As for nitrogen sources, for example, ammonia, ammonium salts such as ammonium sulfate, ammonium chloride, and ammonium nitride, or nitrates may be used. Also, as for inorganic salts, for example, sodium chloride, potassium chloride, potassium phosphate, magnesium sulfate, calcium chloride, calcium nitride, manganese chloride, ferrous sulfate, chromium, and the like may be used. Also, organic components such as peptone, soybean powder, defatted soybean meal, meat extract, and yeast extract may be used.

As for *Bifidobacterium* and/or lactobacilli to be used in the present technology, the culture obtained by culturing may be used as it is, or may be used through dilution or concentration, or microbial cells collected from the culture may be used.

The *Bifidobacterium* and/or the lactobacilli contained as an active ingredient in the composition for reducing body fat and the composition for reducing waist circumference according to the present technology may be one type alone, or may be any combination of two or more types. Also, the composition for reducing body fat or the composition for reducing waist circumference according to the present technology may include only the active ingredient, or may be a composition in which the active ingredient is blended with optional ingredients other than the active ingredient. The optional ingredients are not particularly limited, and additives generally to be blended with medicines or foods may be blended.

(4) Subject

The composition for reducing body fat according to the present technology targets a pre-obese group of subjects or an obese group of subjects, all of whom have intestinal flora in which the ratio of the phylum Firmicutes to the phylum Bacteroidetes has a high value. Also, the composition for reducing waist circumference according to the present technology targets a pre-obese group of subjects or an obese group of subjects, and preferably targets a pre-obese group of subjects or an obese group of subjects, in which the ratio of the phylum Firmicutes to the phylum Bacteroidetes has a high value.

Also, when the ratio of the phylum Firmicutes to the phylum Bacteroidetes has a high value, although there is no particular limitation, the ratio of the phylum Firmicutes to the phylum Bacteroidetes is preferably 1.3 or more, more preferably 1.5 or more, and further preferably 1.7 or more.

(5) Application

The composition for reducing body fat according to the present technology reduces body fat, thereby being useful for a pre-obese group of subjects or an obese group of subjects having obesity-type intestinal flora, and also, the composition for reducing waist circumference according to the present technology reduces the waist circumference, thereby being useful for a pre-obese group of subjects or an obese group of subjects. That is, these compositions may be used for preventing, treating and/or improving obesity.

Also, the composition for reducing body fat according to the present technology promotes decomposition of subcutaneous fat and visceral fat, thereby suppressing differentiation and maturation into subcutaneous fat cells and visceral fat cells. Thus, obesity is prevented or improved. Also, the fasting blood glucose level is also reduced, and then various lifestyle-related diseases that can occur as a result of the obesity are prevented or improved. Therefore, the use in the form of medicines, quasi-drugs, foods and drinks, feeds and the like based on these applications is possible.

Regarding the composition for reducing body fat and the composition for reducing waist circumference according to the present technology, these compositions according to the present technology may be added to medicines, quasi-drugs, foods/drinks, or feeds which are conventionally known, in preparation, or these compositions may be mixed with the raw materials so as to produce new medicines, quasi-drugs, foods/drinks, feeds, or the like.

In the use for medicines, quasi-drugs, foods/drinks, feeds, etc. the composition for reducing body fat or the composition for reducing waist circumference according to the present technology may be used as it is, or after being concentrated, or after being processed into a solid form, a granular form or a powder form. Hereinafter, each application will be described in detail.

(5-1) Medicines, Quasi-Drugs

The composition for reducing body fat and the composition for reducing waist circumference according to the present technology may be used as active ingredients in medicines, quasi-drugs, etc. for humans or animals, after being blended with these, so that the excellent body fat reducing effect or waist circumference reducing effect may be obtained.

Regarding the composition for reducing body fat and the composition for reducing waist circumference according to the present technology, these compositions may be added to conventionally known medicines, quasi-drugs, or the like in preparation, or these compositions may be mixed with the raw materials so as to produce new medicines, quasi-drugs, or the like.

When used in medicines, quasi-drugs, etc., the composition for reducing body fat or the composition for reducing waist circumference according to the present technology may be used as it is, or after being concentrated, or after being processed into a solid form, a granular form or a powder form.

In the case of a medicine, the corresponding medicine may be properly formulated into a desired dosage form according to an administration method such as oral administration or parenteral administration. The dosage form is not particularly limited, but in the case of oral administration, it is possible to perform formulation into, for example, solid preparations such as powder, granules, tablets, troches, and capsules; and liquid preparations such as solutions, syrups, suspensions, and emulsions. In the case of parenteral administration, it is possible to perform formulation into, for example, suppositories, spray, inhalants, ointment, patches, injections, and the like. In the present technology, formulation into a dosage form for oral administration is preferred.

The formulation may be properly carried out according to a dosage form by a conventionally known method.

In the formulation, the formulation may be performed by blending with a proper formulation carrier. Also, in addition to the composition for reducing body fat according to the present technology, components generally used for formulation, such as an excipient, a pH adjuster, a colorant, and a corrigent, may be used. Also, components having an effect of preventing, treating and/or improving diseases or symptoms which are conventionally known or to be found in the future may be properly used in combination depending on the purpose.

As for the formulation carrier, various organic or inorganic carriers may be used depending on the dosage forms.

In the case of solid preparation, examples of the carrier may include excipients, binders, disintegrants, lubricants, stabilizers, and corrigents/flavoring agents, etc.

Examples of the excipient may include sugar derivatives such as lactose, sucrose, glucose, mannitol, and sorbitol; starch derivatives such as cornstarch, potato starch, α-starch, dextrin, and carboxymethyl starch; cellulose derivatives such as crystalline cellulose, hydroxypropyl cellulose, hydroxypropyl methylcellulose, carboxymethyl cellulose, and carboxymethyl cellulose calcium; gum arabic; dextran; pullulan; silicate derivatives such as light anhydrous silicic acid, synthetic aluminum silicate, and magnesium aluminometasilicate; phosphate derivatives such as calcium phosphate; carbonate derivatives such as calcium carbonate; and sulfate derivatives such as calcium sulfate.

Examples of the binder may include gelatin; polyvinylpyrrolidone; macrogol and the like in addition to the excipients.

Examples of the disintegrant may include cellulose derivatives or chemically modified starch such as sodium croscarmellose, sodium carboxymethylstarch, and cross-linked polyvinylpyrrolidone in addition to the excipients.

Examples of the lubricant may include talc; stearic acid; metallic stearates such as calcium stearate, and magnesium stearate; colloidal silica; waxes such as bee gum and spermaceti; boric acid; glycol; carboxylic acids such as fumaric acid and adipic acid; carboxylic acid sodium salts such as sodium benzoate; sulfates such as sodium sulfate; leucine; lauryl sulfates such as sodium lauryl sulfate, and magnesium lauryl sulfate; silicic acids such as silicic acid anhydride, and silicic acid hydrate; and starch derivatives.

Examples of the stabilizer may include paraoxybenzoic acid esters such as methylparaben and propylparaben; alcohols such as chlorobutanol, benzylalcohol, and phenylethylalcohol; benzalkonium chloride; acetic anhydride; and sorbic acid.

Examples of the corrigent/flavoring agent may include sweeteners, acidulants, flavors, etc.

The carrier to be used in the case of liquid preparations for oral administration may include a solvent such as water, a corrigent/flavoring agent, etc.

Also, the composition for reducing body fat or the composition for reducing waist circumference according to the present technology may also be used in combination with a medicine or the like having a body fat reducing action or a waist circumference reducing action which is conventionally known or to be found in the future.

Through the composition for reducing body fat and the composition for reducing waist circumference according to the present technology, it is possible to prevent, treat and/or improve obesity (also called an "obesity disease"). Also, the composition for reducing body fat and the composition for reducing waist circumference according to the present technology may also prevent, treat and/or improve diseases caused by the obesity. Such a disease is not particularly limited, but examples thereof may include metabolic syndromes, diabetes (including type 2 diabetes), hyperlipidaemia, hypertension, arteriosclerosis, etc. The composition for reducing body fat and the composition for reducing waist circumference according to the present technology may be used for preventing, treating and/or improving these diseases and symptoms. Accordingly, the present technology may also provide a composition for preventing, treating and/or improving the diseases.

The amount of *Bifidobacterium* and/or lactobacilli in a composition is not particularly limited, but it is preferable to be present in such an amount that a daily dose may be ingested without difficulty, and it is more preferable to contain $1 \times 10^3$ to $1 \times 10^{12}$ CFU/g. Also, it is desirable that the daily dose is at least $1 \times 10^3$ CFU/day or more, more preferably $1 \times 10^6$ CFU/day or more, more preferably $1 \times 10^8$ CFU/day or more, more preferably $2 \times 10^{10}$ CFU/day or more, or more.

CFU indicates a unit for colony formation: a colony forming unit. When microbial cells are dead bacteria, cfu/g or cfu/ml may be replaced with individual cells/g or individual cells/ml. When the present microbial cells are a crushed product, it is possible to express the number of bacteria (individual cells/g) before crushing, in terms of weight.

The daily dose of the medicine may be taken once or divided into multiple times per day. The subject that the dose is administered to is generally a human, but in the present technology, mammals other than humans, for example, pets such as dogs and cats, and domestic animals such as cows, sheep, and pigs, are also included.

(5-2) Foods and Drinks

The composition for reducing body fat and the composition for reducing waist circumference according to the present technology may be used as active ingredients in health foods, functional foods, patient foods, enteral nutritional foods, special purpose foods, and health functional foods, for humans or animals (which have a concept of applications for body fat reduction or for waist circumference reduction), and foods for specified health uses, functionality labeled foods, and nutritionally functional foods (labeled with the above described application or the like) after being blended with these, so that the excellent body fat reducing effect or waist circumference reducing effect may be used.

In the case of foods or drinks, the corresponding food or drink may have any form such as liquids, pastes, solids, or powder, and may be not only tablet confectionaries, liquid foods, and feeds (including the use for pets), but also, for example, flour products, instant foods, processed agricultural products, processed seafood products, processed livestock products, milk•dairy products, oils and fats, basic seasonings, complex seasonings•foods, frozen foods, confectioneries, drinks, and commercially available foods other than these.

Examples of the dairy product may include fermented milk, milk drinks, lactic beverages, sweetened condensed milk, skim milk powder, sweetened milk powder, modified milk powder, cream, cheese, butter, ice creams, etc.

Examples of the flour product may include bread, macaroni, spaghetti, noodles, cake mix, frying powder, bread crumbs, etc.

Examples of the instant food may include instant noodles, cup noodles, retort•cooked foods, cooked cans, microwave foods, instant soup•stew, instant miso soup•soup, canned soup, freeze•dried foods, other instant foods, etc.

Examples of the processed agricultural product may include canned agricultural products, canned fruits, jams•marmalades, pickles, boiled beans, dried agricultural products, cereals (processed grain products), etc.

Examples of the processed seafood product may include canned seafoods, fish-flesh hams•sausages, seafood paste products, seafood delicacies, tsukudani, etc.

Examples of the processed livestock product may include canned livestock•pastes, meat hams•sausages, etc.

Examples of the oil and fat may include butter, margarines, vegetable oils, etc.

Examples of the basic seasoning may include soy sauces, miso, sauces, processed tomato seasonings, mirins, vinegars, etc.

Examples of the complex seasoning•food may include cooking mix, curry sauces, spicy soy sauces, dressings, mentsuyu, spices, other complex seasonings, etc.

Examples of the frozen food may include frozen food ingredients, semi-cooked frozen foods, cooked frozen foods, etc.

Examples of the confectionery may include caramels, candies, chewing gums, chocolates, cookies, biscuits, cakes, pies, snacks, crackers, Japanese sweets, rice confectionaries, bean confectionaries, dessert confectioneries, other confectionaries, etc.

Examples of the drink may include carbonated drinks, natural fruit juices, fruit juice drinks, fruit juice-containing soft drinks, pulp drinks, granule-containing fruit drinks, vegetable-based drinks, soymilk, soymilk drinks, coffee drinks, tea drinks, powdered drinks, concentrated drinks, sports drinks, nutritional drinks, alcohol drinks, other favorite drinks, etc.

Examples of the other commercial foods may include weaning foods, furikake, ochazuke seaweed, etc.

In the present technology, the action of "labeling" includes all actions of informing consumers of the above described application, and all expressions corresponding to the action of "labeling" of the present technology regardless of the purpose of a label, the contents of a label, and a target object and a medium of labeling as long as the application for body fat reduction or the like may be recalled and analogized.

Also, it is desirable that "labeling" is made by an expression that allows the consumers to directly recognize the application. Specifically, an action of assignment and delivery of a product or a product packaging related to a food or a drink (on which the application is described), and display and importation for the assignment or delivery; and an action of displaying or distributing advertisements, a price list, or a transaction document related to the product, on which the application is described, or providing information having these as contents, on which the application is described, by an electromagnetic (for example, the Internet, etc.) method may be mentioned.

Meanwhile, as for the label contents, a label permitted by the government or the like (for example, a label or the like that is approved in accordance with various systems specified by the government, and is applied in the form based on such approval) is preferred. Also, it is desirable that such label contents are attached to packaging, containers, catalogs, pamphlets, advertising materials at a sales site such as point of purchase advertising (POP), other documents, and the like.

Also, as for the "label," labels for health foods, functional foods, patient foods, enteral nutritional foods, special purpose foods, health functional foods, foods for specified health uses, functionality labeled foods, nutritionally functional foods, quasi-drugs, etc. may also be exemplified. Among these, particularly, labels approved by the Consumer Affairs Agency, for example, labels or the like approved by systems for foods for specified health uses, systems for functionality labeled foods, and systems similar to these, may be exemplified. More specifically, labels for foods for specified health uses, labels for foods for conditional specified health uses, labels for functionality labeled foods, labels to the effect that the structure or function of a body is affected, labels on disease risk reduction, and the like may be exemplified. Among these, as a typical example, labels for foods for specified health uses, which are stipulated in the Enforcement Regulations of Health Promotion Law (Apr. 30, 2003, Japanese Ministry of Health, Labor and Welfare Ordinance No. 86) (particularly, labels for health applications), labels for functionality labeled foods, which are stipulated in Food Labeling Act (2013, Law No. 70), labels similar thereto and the like may be exemplified.

Words used for the above described labeling are not limited to only words for body fat reduction, waist circumference reduction, or the like. It is needless to say that even other words are included in the scope of the present technology as long as they are words indicating the effect of prevention, treatment and/or improvement of various diseases or symptoms related to body fat reduction or waist circumference reduction. Examples of these words may include "for those who have obesity signs," "for those who are worried about belly fat," "for those who are worried about body weight," "for those who are worried about body fat," "reducing waist circumference," "for those who are worried about waist circumference," and the like, and it is also possible to perform labeling based on various applications, which allows consumers to recognize the effect of body fat reduction or waist circumference reduction.

(5-3) Feeds

The composition for reducing body fat and the composition for reducing waist circumference according to the present technology may be used as active ingredients in feeds for animals after being blended with these, so that the excellent body fat reducing effect or waist circumference reducing effect may be obtained.

Examples of raw materials of the feed may include: cereals such as corn, wheat, barley, and rye; brans such as wheat bran, barley bran, rice bran, and defatted rice bran; production dregs such as corn gluten meal, and corn jam meal; animal feeds such as skim milk powder, whey, fish meal, and bone meal; yeasts such as beer yeast; mineral feeds such as calcium phosphate, and calcium carbonate; oils and fats; amino acids; and sugars. Also, examples of the form of the feed may include pet feeds (pet foods and the like), livestock feeds, fish feeds, and the like.

The amount of bacteria belonging to *Bifidobacterium breve* in the feed according to the present technology may be freely set according to the body weight, etc. as long as the effect of the present technology is not impaired.

The amount of the present microbial cells in a feed composition is properly set according to dosage forms, usage, subject age, sex, diseases or syndromes, types of symptoms or disorders, degrees thereof, other conditions, and the like. However, in general, the amount of *Bifidobacterium* and/or lactobacilli is not particularly limited, but it is preferable to be present in such an amount that a daily dose may be ingested without difficulty, and it is more preferable to contain $1 \times 10^3$ to $1 \times 10^{12}$ CFU/g. Also, it is desirable that the daily dose is at least $1 \times 10^3$ CFU/day or more, more preferably $1 \times 10^6$ CFU/day or more, more preferably $1 \times 10^8$ CFU/day or more, more preferably $2 \times 10^{10}$ CFU/day or more, or more.

When the present microbial cells are dead bacteria, cfu/g or cfu/ml may be replaced with individual cells/g or individual cells/ml. When the present microbial cells are a crushed product, cfu/g or cfu/ml, or individual cells/g or individual cells/ml may be replaced with a crushed product of live bacteria or dead bacteria of above cfu/g or cfu/ml or individual cells/g or individual cells/ml.

<2. Method of Selecting Probiotic Bacteria Having Anti-Obesity Action>

A method of selecting probiotic bacteria having an anti-obesity action according to the present technology (hereinafter, also simply referred to as a "selection method A according to the present technology") includes at least (1) a step classifying into two groups subjects in which the ratio of the phylum Firmicutes to the phylum Bacteroidetes has a high value, called group (a), subjects not belonging to group (a), called group (b), by measuring the ratio of intestinal flora of the subjects at a phylum level (hereinafter, also simply called step (A-1)), (2) a step of administering probiotic bacteria to each of the subjects in both groups classified in the step (1) (hereinafter, also simply called a step (A-2)), and (3) a step of measuring body fat of the subjects in each group (hereinafter, also simply called a step (A-3)), in which probiotic bacteria having an anti-obesity action on the subjects in group (a) or (b) are selected. Hereinafter, each step will be described in detail.

(1) Step (A-1)

In the step (A-1), composition ratios of intestinal flora of a subject are measured at a phylum level, and classification into groups such as a group (a) in which the ratio of the phylum Firmicutes to the phylum Bacteroidetes has a high value, and a group (b) not belonging to the group (a) is performed.

The subject is generally a human, but in the present technology, mammals other than humans, for example, pets such as dogs and cats, and domestic animals such as cows, sheep, and pigs are also included.

A method of measuring composition ratios of intestinal flora at a phylum level (for example, five phyla of the phylum Firmicutes, the phylum Bacteroidetes, the phylum Actinobacteria, the phylum Fusobacteria, and the phylum Proteobacteria) is not particularly limited, but, for example, a method performed by a hierarchical clustering analysis based on the Pearson's correlation coefficient by using MeV (Multiple Experiment Viewer) 4.9.0 may be exemplified.

Also, in the method of the hierarchical clustering analysis, in addition to MeV, SAS, SPSS, Stata, R, Excel, or other statistical analysis software, or a data analysis method that is available on the Internet, or may be analyzed on the Internet may be used to calculate a distance between clusters. As the method of measuring a distance between clusters, in addition to the Pearson's correlation coefficient, options such as a nearest-neighbor method, a furthest-neighbor method, a center of gravity method, and a ward method may be exemplified.

As a cluster classification method, in addition to the ratio of the phylum Firmicutes to the phylum Bacteroidetes, a classification method by a ratio of bacteria of the genus *Ruminococcus*, or bacteria of the genus *Prevotella* to the phylum Bacteroidetes, a classification method by occupancy ratios of the genus *Clostridium*, the genus *Enterococcus*, the genus *Bifidobacterium*, and the genus *Akkermancia* through a genus level analysis, and a classification method by occupancy ratios of *Akkermancia muciniphila* species, and Bacteroidetes *thetaiotaomicron* species through a species level analysis may be exemplified.

The group (a) is not particularly limited as long as the ratio of the phylum Firmicutes to the phylum Bacteroidetes has a high value, but the ratio of the phylum Firmicutes to the phylum Bacteroidetes is preferably 1.3 or more, more preferably 1.5 or more, and further preferably 1.7 or more.

Also, it is desirable that the group (a) is a pre-obesity group of subjects or an obese group of subjects having obesity-type intestinal flora. Specifically, the same are enumerated in <1. Composition>.

(2) Step (A-2)

In the step (A-2), probiotic bacteria are administered to each of the groups classified in the step (1).

The probiotic bacteria are not particularly limited, but *Bifidobacterium* and/or lactobacilli are preferred.

Also, in the selection method A according to the present technology, it is preferable to use *Bifidobacterium* enumerated in <1. Composition>, as for the *Bifidobacterium*. Also, among these, it is particularly preferable to use *Bifidobacterium breve*.

As for the *Bifidobacterium breve*, specifically, similarly to those enumerated in <1. Composition>, it is preferable to use *Bifidobacterium breve* MCC1274 (FERN BP-11175) and/or *Bifidobacterium breve* M-16V (NITE BP-02622).

In the selection method A according to the present technology, as for the *Bifidobacterium breve*, it is particularly preferable to use *Bifidobacterium breve* MCC1274 (FERM BP-11175).

Also, in the selection method A according to the present technology, it is preferable to use lactobacilli enumerated in <1. Composition>, as for the lactobacilli.

An administration method is not particularly limited, and methods such as oral administration or parenteral administration may be employed. However, in the present technology, oral administration is particularly preferable. Also, an administration form is also not particularly limited, and tablets, capsules, powder, milk powder, oil drops, fermented milk, dairy products, beverages, confectioneries, feeds, or the like containing, for example, 1 to 30 billion probiotic bacteria are administered once to three divided times per day.

(3) Step (A-3)

In the step (A-3), in each group of subjects (the groups (a) and (b)), body fat of the subjects is measured.

The body fat measuring method is not particularly limited, and, for example, a conventional body composition measuring device or the like is used for measurement.

In the selection method A according to the present technology, by performing the steps (A-1) to (A-3), probiotic bacteria having an anti-obesity action on the subjects of groups (a) or (b) are selected. The "anti-obesity action" as mentioned herein refers to a body fat reducing action before administration of probiotic bacteria and after the administration. Also, as necessary, the selection method A according to the present technology may include other steps.

In the selection method A according to the present technology, by selecting any of the subjects in groups (a) and (b) as one in which body fat is being reduced, it is possible to find a group of subjects whose body fat can be reduced and to help prevention, treatment and/or improvement of obesity.

In the present technology, it is desirable to select probiotic bacteria having an anti-obesity action on the subjects of group (a). This is because it can be said that the subjects of group (a) have obesity-type intestinal flora since the ratio of the phylum Firmicutes to the phylum Bacteroidetes has a high value, and it is possible to help prevention, treatment and/or improvement of obesity by selecting probiotic bacteria having an anti-obesity action on the corresponding group.

<3. Method of Selecting Responders to Probiotic Bacteria having Anti-Obesity Action>

In a method of selecting responders to probiotic bacteria having an anti-obesity action according to the present technology (hereinafter, also simply referred to as a "selection method B according to the present technology"), at least through (1) a step of administering probiotic bacteria having an anti-obesity action to a subject (hereinafter, also simply called a step (B-1)), and (2) a step of classifying into groups such as a group (c), subjects in which body fat is significantly reduced, and a group (d) not belonging to the group (c) (hereinafter, also simply referred to as a step (B-2)), responders to probiotic bacteria having the anti-obesity action are selected. Hereinafter, each step will be described in detail.

(1) Step (B-1)

In the step (B-1), probiotic bacteria having an anti-obesity action are administered to a subject. The "anti-obesity action" as mentioned herein refers to an action of reducing body fat by administration of probiotic bacteria, as compared to when the corresponding probiotic bacteria are not administered.

The probiotic bacteria having an anti-obesity action are not particularly limited, but *Bifidobacterium* and/or lactobacilli are preferred.

Also, in the selection method B according to the present technology, it is preferable to use *Bifidobacterium* enumerated in <1. Composition>, as for the *Bifidobacterium*. Also, among these, it is particularly preferable to use *Bifidobacterium breve*.

As for the *Bifidobacterium breve*, specifically, similarly to those enumerated in <1. Composition>, it is preferable to use *Bifidobacterium breve* MCC1274 (FERN BP-11175) and/or *Bifidobacterium breve* M-16V (NITE BP-02622).

In the selection method B according to the present technology, as for the *Bifidobacterium breve*, it is particularly preferable to use *Bifidobacterium breve* MCC1274 (FERM BP-11175).

Also, in the selection method B according to the present technology, as for the lactobacilli, it is preferable to use lactobacilli enumerated in <1. Composition>.

More specifically, as for the probiotic bacteria having an anti-obesity action, *Bifidobacterium breve* MCC1274 (FERM BP-11175), *Bifidobacterium longum* BB536 (ATCC BAA-999) *Lactobacillus amylovorus* CP1563, *Lactobacillus gasseri* SBT2055 (LG2055), *Bifidobacterium lactis* Bb-122 (*Bifidobacterium animalis* subsp. *lactis* BB-12), *Lactobacillus casei* Shirota, VSL #3, *Lactobacillus rhamnosus* GG (ATCC53103), *Lactobacillus rhamnosus* CGMCC1. 3724 (LPR), *Lactobacillus gasseri* BNR17, *Bifidobacterium animalis* ssp. *lactis* 420, *Akkermansia muciniphila*, Bacteroidetes *uniformis* CECT 7771, Bifidobacteria L66-5, L75-4, M13-4 and FS31-12, *Bifidobacterium animalis* subsp. *lactis* I-2494, *Bifidobacterium animalis* subsp. *lactis* LMG P-28149, *Bifidobacterium breve* CNCM 1-4035, *Bifidobacterium longum* SPM 1207, *Bifidobacterium pseudocatenulatum* SPM 1204, *Lactobacillus acidophilus* L1, *Lactobacillus acidophilus* LA5, *Lactobacillus acidophilus* NCFM, *Lactobacillus brevis* OK56, *Lactobacillus casei* DN001, *Lactobacillus casei* NCDC 19, *Lactobacillus coryniformis* CECT5711, *Lactobacillus curvatus* HY7601, *Lactobacillus fermentum* PCC, *Lactobacillus* JBD301, *Lactobacillus paracasei* CNCM 1-4034, *Lactobacillus paracasei* CNCM 1-4270, *Lactobacillus paracasei* F19, *Lactobacillus paracasei* Lpc-37, *Lactobacillus planetarium* A7, *Lactobacillus plantarum* HAC01, *Lactobacillus plantarum* KY1034, *Lactobacillus plantarum*SN13T, *Lactobacillus plantarum* TENSIA, *Lactobacillus reuteri* NCIMB 30242, *Lactobacillus reuteri* SD5865, *Lactobacillus reuteri* strain NCIMB 30242, *Lactobacillus rhamnosus*CNCM, *Lactobacillus rhamnosus* 1-3690, *Lactobacillus rhamnosus* LMG S-28148, *Lactobacillus rhamnosus* NCDC17, *Lactobacillus salivarium* UCC118, *Lactobacillus salivarium*33, *Lactobacillus salivarius* Ls-33, *Lactobacillus salivarius* UBL S22, *Pediococcus pentosaceus* LP28, *Saccharomyces boulardii* Biocodex, or the like may be employed. In the present technology, among these, one type may be used alone, or any combination of two or more types may be used.

The subject is generally a human, but in the present technology, mammals other than humans, for example, pets such as dogs and cats, and domestic animals such as cows, sheep, pigs, and horses, are also included.

An administration method is not particularly limited, and methods such as oral administration or parenteral administration may be employed. However, in the present technology, oral administration is particularly preferable. Also, an administration form is also not particularly limited, and tablets, capsules, powder, milk powder, oil drops, fermented milk, dairy products, beverages, confectioneries, feeds, or the like containing, for example, 1 to 30 billion probiotic bacteria are administered once to three divided times per day.

(2) Step (B-2)

In the step (B-2), classification of subjects into groups such as a group (c), wherein subject's body fat is significantly reduced, and a group (d) not belonging to the group (c) is performed.

It is preferable that the group (c) is, for example, a pre-obese group of subjects or an obese group of subjects having obesity-type intestinal flora. Examples of the obesity-type intestinal flora may include intestinal flora in which the ratio of the phylum Firmicutes to the phylum Bacteroidetes has a high value, intestinal flora in which the ratio of genus *Prevotella* to the phylum Bacteroidetes has a high value, intestinal flora in which the ratio of genus *Ruminococcus* to the phylum Bacteroidetes has a high value, intestinal flora having the phylum Firmicutes in a large amount, intestinal flora having the phylum Bacteroidetes in a small amount, intestinal flora having the genus *Ruminococcus* in a large amount, intestinal flora having the genus *clostridium* in a large amount, enterobacteria having the genus *Enterococcus* in a large amount, intestinal flora having the genus *Bifidobacterium* in a small amount, intestinal flora having the genus *Akkermancia* in a small amount, intestinal flora having the species *Akkermansia muciniphila* in a small amount, intestinal flora having the species Bacteroidetes *thetaiotaomicron* in a small amount, and intestinal flora with low abundance or diversity in evaluation by a chaol index, a Shannon index, a shimpson index, or the like.

In the present technology, among these, as for the obesity-type intestinal flora, intestinal flora in which the ratio of the phylum. Firmicutes to the phylum Bacteroidetes has a high value is preferred in the pre-obesity group or the obese patients.

Also, in this case, the ratio of the phylum Firmicutes to the phylum Bacteroidetes is preferably 1.3 or more, more preferably 1.5 or more, and further preferably 1.7 or more. Accordingly, it is possible to efficiently select responders to probiotic bacteria having the anti-obesity action.

Also, it is preferable that the group (c) subjects are a pre-obese group or an obese group having obesity-type intestinal flora. Specifically, the same are enumerated in <1. Composition>.

In the selection method B according to the present technology, by performing the steps (B-1) to (B-2), responders to probiotic bacteria having the anti-obesity action are selected. In the selection method B according to the present technology, the subjects of group (c) are responders, and the subjects of group (d) (the group not belonging to the group (c)) are non-responders. Also, as necessary, the selection method B according to the present technology may include other steps such as a step of measuring body fat of a subject.

In the selection method B according to the present technology, by selecting responders to probiotic bacteria having the anti-obesity action, it is possible to find a group whose body fat can be reduced, and to help prevention, treatment and/or improvement of obesity.

In the present technology, it is possible to employ the following configurations.

[1] A composition for reducing body fat, which contains *Bifidobacterium* and/or lactobacilli as an active ingredient, and is used for a pre-obesity group or obese patients having intestinal flora in which the ratio of the phylum Firmicutes to the phylum Bacteroidetes has a high value.

[2] In the composition for reducing body fat described in [1], the ratio of the phylum Firmicutes to the phylum Bacteroidetes is 1.3 or more.

[3] In the composition for reducing body fat described in [1] or [2], the *Bifidobacterium* are any one or more types of a group including *Bifidobacterium longum* subspecies *longum*, *Bifidobacterium bifidum*, *Bifidobacterium breve*, *Bifidobacterium longum* subspecies *infantis*, *Bifidobacterium adolescentis*, *Bifidobacterium catenulatum*, *Bifidobacterium pseudocatenulatum*, *Bifidobacterium animalis* subspecies *animalis*, and *Bifidobacterium animalis* subspecies *lactis*.

[4] In the composition for reducing body fat described in [3], the *Bifidobacterium breve* is *Bifidobacterium breve* MCC1274 (FERN BP-11175).

[5] Use of *Bifidobacterium* and/or lactobacilli in a body fat reducing composition used for a pre-obesity group or obese patients having intestinal flora in which the ratio of the phylum Firmicutes to the phylum Bacteroidetes has a high value.

[6] Use of *Bifidobacterium* and/or lactobacilli in producing a body fat reducing composition used for a pre-obesity group or obese patients having intestinal flora in which the ratio of the phylum Firmicutes to the phylum Bacteroidetes has a high value.

[7] A method of preventing, treating and/or improving a pre-obesity group or obese patients having intestinal flora in which the ratio of the phylum Firmicutes to the phylum Bacteroidetes has a high value, by *Bifidobacterium* and/or lactobacilli as an active ingredient.

[8] A method including at least (1) a step of performing classification into groups such as a group (a) in which the ratio of the phylum Firmicutes to the phylum Bacteroidetes has a high value, and a group (b) not belonging to the group (a), by clustering composition ratios of intestinal flora of a subject at a phylum level, (2) a step of administering probiotic bacteria to each of the groups classified in the step (1), and (3) a step of measuring body fat of each group, in which probiotic bacteria having an anti-obesity action on the group (a) or (b) are selected.

[9] A method of selecting responders to probiotic bacteria having an anti-obesity action at least through (1) a step of administering probiotic bacteria having the anti-obesity action to a subject, and (2) a step of performing classification into groups such as a group (c) in which the ratio of the phylum. Firmicutes to the phylum Bacteroidetes has a high value, and a group (d) not belonging to the group (c), by clustering composition ratios of intestinal flora of the subject at a phylum level.

[10] In the method described in [8] or [9], in the group, the ratio of the phylum Firmicutes to the phylum Bacteroidetes is 1.3 or more.

[11] In the method described in any one of [8] to [10], the probiotic bacteria are *Bifidobacterium* and/or lactobacilli.

[12] In the method described in [11], the *Bifidobacterium* are anyone or more types of a group including *Bifidobacterium longum* subspecies *longum*, *Bifidobacterium bifidum*, *Bifidobacterium breve*, *Bifidobacterium longum* subspecies *infantis*, *Bifidobacterium adolescentis*, *Bifidobacterium catenulatum*, *Bifidobacterium pseudocatenulatum*, *Bifidobacterium animalis* subspecies *animalis*, and *Bifidobacterium animalis* subspecies *lactis*.

[13] In the method described in [12], the *Bifidobacterium breve* is *Bifidobacterium breve* MCC1274 (FERN BP-11175).

[14] In the method described in [11], the lactobacilli are any one or more types of a group including *Lactobacillus plantarum*, *Lactobacillus casei*, *Lactobacillus acidophilus*, *Lactobacillus delbrueckii* subspecies *bulgaricus*, *Lactobacillus gasseri*, *Lactobacillus amylovora*, *Lactobacillus reuteri*, *Lactobacillus rhamnosus*, *Lactobacillus paracasei*, *Lactobacillus fermentum*, *Lactobacillus salivarius*, and *Lactobacillus lactis*.

[15] Use of *Bifidobacterium* and/or lactobacilli in a waist circumference reducing composition used for a pre-obesity group or obese patients.

[16] Use of *Bifidobacterium* and/or lactobacilli in producing a waist circumference reducing composition used for a pre-obesity group or obese patients.

EXAMPLES

Hereinafter, the present technology will be described on the basis of Examples.

Examples described below are described as examples of a representative Example of the present technology, by which the scope of the present technology is not narrowly analyzed.

Example 1

In this Example 1, a test for humans was carried out to verify a body fat reducing action and a waist circumference reducing action by ingestion of *Bifidobacterium breve* MCC1274 and to verify changes in intestinal flora and body fat of each individual.

1. Test Method (1) Subject

In this test, a randomized, double-blind, placebo-controlled intergroup comparison test was performed on 80 adult males and females aged 20 to 64 with a 1 obesity grade (the BMI value is 25 kg/m² or more and less than 30 kg/m²), as subjects. The subjects received consent forms on participation in this test from all cases before the test start. It was confirmed that the subjects were healthy people and did not correspond to the following exclusion criteria.

Exclusion Criteria (i) A person who is being treated for a serious disease, etc. (*1) or a person having such a serious medical history

*1 Diseases such as a cerebrovascular disease, a heart disease, a liver disease, a digestive system disease, endocrine and metabolic diseases, and a sleep apnea syndrome.

(ii) A person who is suffering from a gastrointestinal disease, and is taking medication (iii) A person who is receiving drug treatment for a lifestyle-related disease (diabetes, hypertension, or dyslipidemia)

(iv) A person having a medical history of drug allergy or serious food allergy (v) A pregnant person, a person who is willing to be pregnant during a test period, or a breast-feeding person (vi) a heavy smoker (*2), a heavy drinker (*3), or a person with irregular lifestyles

*2 refers to smoking about 21 or more cigarettes per day
*3 refers to a person who consumes 540 or more ml (about 60 g of pure alcohol) per day on average in terms of Sake.

(vii) A person who is judged to be unsuitable as a subject by a doctor responsible for the test or a doctor in charge of the test, on the basis of the subject background, physical findings, or results of interview, etc.

(2) Allocation Method

The subjects were allocated to a test food intake group (40), and a control food intake group (40) by a stratified permutation block method such that the sex, the age, the BMI value, and the visceral fat area were not biased.

(3) Test Food

The test food intake group ingested two capsules containing 10 billion freeze-dried *Bifidobacterium breve* MCC1274 after each meal, and the control food intake group ingested capsules in which corn starch was blended instead of the freeze-dried microbial powder of Bifidobacteria. Before the test start and at the test end, it was confirmed that the test food and the control food were indistinguishable.

(4) Test Outline

The ingestion period of the test food and the control food was 12 weeks, and the test was performed from September to December (autumn to winter). For the two groups, before ingestion of the test food and the control food for the day on the test food ingestion start date, $0^{th}$ week was set. Then, at the time of the $4^{th}$ week, $8^{th}$ week, and $12^{th}$ week from the ingestion start date, a visit inspection was performed, and evaluation items of a body composition were measured.

As for evaluation items of a body composition, a total fat area of abdomen, a visceral fat area, a subcutaneous fat area, a body weight, a body fat amount, a body fat percentage, a BMI value, and an abdomen circumference (waist circumference) were measured.

The total fat area of abdomen, the visceral fat area, and the subcutaneous fat area were measured by using a dual scan HDS-2000 (manufactured by Omron Healthcare) device. The body weight, the body fat amount, and the body fat percentage were measured by using a medical-grade body composition measuring device In body 770 (manufactured by InBody) by a bioelectrical impedance method. Also, the BMI value was automatically calculated by In Body 770 by using a manually measured height value.

At the $0^{th}$ week and the $12^{th}$ week, in addition to the measurement of a body composition, blood collection and stool collection were performed, and the following blood test and the intestinal flora analysis were performed.

Also, in the blood test, blood lipids (total cholesterol, HDL-cholesterol, LDL-cholesterol, and triglyceride), relation with blood glucose (fasting blood glucose, HbAlc, glycoalbumin, and fasting insulin), liver functions (AST, ALT, γ-GTP, and ALP), and concentrations of inflammation markers (high sensitivity CRP, and LPB; Lipopolysaccharide binding protein) were measured.

Intestinal Flora Analysis

By the following method, DNA was extracted from a stool sample and the intestinal flora analysis was performed.

By using 0.5 mL of fecal suspension from a collected stool sample (a brush-type stool collection kit manufactured by Techno Suruga), DNA was extracted using a bead crushing method. After centrifugation at 14,000×g for 5 min, 400 µL of supernatant was extracted with phenol chloroform, and 250 µL of supernatant was precipitated with isopropanol, and then DNA was collected.

In the extracted DNA, a V3-V4 region included in the 16S rRNA sequence of the bacterial DNA was amplified by a PCR method using a TaKaRa Ex Taq HS Kit (manufactured by Takara), a Tru357F primer:

```
(5'-CGCTCTTCCGATCTCTGTACGGRAGGCAGCAG-3:

sequence No. 1),
``` and a Tru806R primer:

```
(5'-CGCTCTTCCGATCTGACGGACTACHVGGGTWTCTAAT-3':

sequence No. 2).
```

The obtained DNA was purified by using a QIAxcel system (manufactured by QIAGEN), and then was subjected to PCR by using barcode primers for IlluminaMiSeq measurement, Fwd:

```
                                    (sequence No. 3)
5'-AATGATACGGCGACCACCGAGATCTACACNNNNNNNNACAC

TCTTTCCCTACACGACGCTCTTCCGATCTCTG-3',
``` and Rev:

```
                                    (sequence No. 4)
5'-CAAGCAGAAGACGGCATACGAGATNNNNNNNNGTGACTGG

AGTTCAGACGTGTGCTCTTCCGATCTGAC-3'
```

(N is a barcode sequence varying according to each sample, and is A, C, G or T). After purification using a QIAxcel system and a GeneRead Size Selection Kit (manufactured by Qiagen), a sequence analysis was performed with Miseq by using a Miseq v3 Reagent Kit (manufactured by Illumina).

Sequences satisfying the following exclusion criteria were removed from the obtained sequence information, and sequence information connecting sequences was obtained by using fastq-join (version. 1. 1. 2-537).

Exclusion Criteria (i) A human genome sequence and a PhiX 174 sequence added to control (ii) Among sequences not excluded in the above (i), a sequence having a PHRED quality score (hereinafter Q) of 17 or less on the base sequence 3' side (iii) Among sequences not excluded in the above (ii), a sequence of 150 bp or less, a sequence of Q25 or less as a whole, and a sequence not forming a pair Regarding the sequence data, composition ratios of intestinal flora of each subject were analyzed by using QIIME software version 1.8.0 before the test start ($0^{th}$ week) and at the test end ($12^{th}$ week), for each biological grade (Phylum/Division•Class•Order•Family•Genus).

Statistical Analysis

Regarding the statistical analysis of a body composition and blood test results, for comparison between groups, at each evaluation time point after ingestion, the change in amount from the pre-ingestion value was evaluated by an unpaired t-test. For comparison within a group, at each evaluation time point, a change from the pre-ingestion value was evaluated by a paired t-test. A significance level was set to be less than 5%.

2. Test Result

In this test, no subject dropped out, and all 80 subjects completed food ingestion of a target food for 12 weeks, and visit inspection every 4 weeks. Therefore, an efficacy analysis was performed on all 80 subjects participating in the test.

Change of Body Composition

In the control food group, the body fat percentage significantly increased at the $4^{th}$ week, $8^{th}$ week, and $12^{th}$ week after ingestion as compared to that at the baseline ($0^{th}$ week). In the test food group, the body fat percentage significantly reduced at the $8^{th}$ week, and $12^{th}$ week as compared to that in the control food group. Also, similarly to the body fat percentage, the body fat amount also significantly reduced at the $8^{th}$ week, and $12^{th}$ week of ingestion as compared to that in the control group.

Main changes in amounts of a body composition ($12^{th}$ week-$0^{th}$ week) are noted in Table 1 below. More specifically, the following Table 1 illustrates the results of the overall analysis (80 people) and the results of a group 2 (a responder group) to be described below, regarding change amounts (variation values from the $0^{th}$ week) of a body weight, a body fat amount, a body fat percentage, a visceral fat area, a total fat area, a ratio of visceral fat/subcutaneous fat, a fasting blood glucose, and a waist circumference after a test food was ingested for 12 weeks.

TABLE 1

|  | Overall Analysis | | Responder Group | |
| --- | --- | --- | --- | --- |
|  | Control Group (n = 40) | Test Group (n = 40) | Control Group (n = 11) | Test Group (n = 10) |
| Body Weight (kg) | 0.5 ± 1.5 | 0.3 ± 1.6 | 1.4 ± 1.4 | −0.2 ± 1.8 * |
| Body Fat Amount (kg) | 0.6 ± 1.4 | 0.0 ± 1.0 * | 1.3 ± 1.0 | −0.1 ± 1.3 * |
| Body Fat Percentage (%) | 0.6 ± 1.4 | −0.1 ± 1.0 * | 1.0 ± 1.2 | −0.03 ± 1.2 * |
| Visceral Fat Area (cm$^2$) | 2.6 ± 8.7 | −0.0 ± 10.0 | 6.2 ± 6.8 | −9.9 ± 7.7 ** |
| Total Fat Area (cm$^2$) | 4.1 ± 21.3 | 3.0 ± 24.8 | 10.8 ± 14.3 | −10.4 ± 29.9 # |
| Ratio of Visceral Fat/Subcutaneous Fat | 0.010 ± 0.037 | −0.003 ± 0.047 | 0.021 ± 0.039 | −0.037 ± 0.041 ** |
| Fasting Blood Glucose (mg/dL) | 0.88 ± 5.9 | 0.50 ± 7.8 | 3.4 ± 4.3 | −3.3 ± 5.9 ** |
| Waist Circumference (cm) | −0.1 ± 4.1 | −1.1 ± 2.4 | 0.9 ± 4.0 | −1.2 ± 2.5 |

# P < 0.1, * P < 0.05, ** P < 0.01, Significant Inter-Group Difference Verification for Control Group and Test Group
At 12th week after ingestion, change amount is expressed by mean ± SD Also, in the results of the overall analysis and the group 2 (the responder group) to be described below, respectively, for each measurement item, the change rate obtained by dividing a difference in a change amount from the placebo group, by the baseline $0^{th}$ week value is noted in Table 2 below.

TABLE 2

|  | Overall Analysis | | | Responder Group | | |
| --- | --- | --- | --- | --- | --- | --- |
|  | $0^{th}$ Week Average Value | Inter-Group Difference of Change Amount | Change Rate | $0^{th}$ Week Average Value | Inter-Group Difference of Change Amount | Change Rate |
| Body Weight (kg) | 80.6 | −0.2 | Reduction By 0.2% | 80.9 | −1.6 | Reduction By 2.0% |
| Body Fat Amount (kg) | 22.8 | −0.6 | Reduction By 2.6% | 23.3 | −1.4 | Reduction By 6.0% |
| Body Fat Percentage (%) | 28.3 | −0.7 | Reduction By 2.5% | 28.7 | −1.03 | Reduction By 3.6% |
| Visceral Fat Area (cm$^2$) | 103.6 | −2.6 | Reduction By 2.5% | 102.7 | −16.1 | Reduction By 15.6% |
| Total Fat Area (cm$^2$) | 338.9 | −1.1 | Reduction By 0.3% | 347.1 | −21.2 | Reduction By 6.1% |
| Ratio of Visceral Fat/Subcutaneous Fat | 0.446 | −0.003 | Reduction By 0.7% | 0.426 | −0.058 | Reduction By 13.6% |
| Fasting Blood Glucose (mg/dL) | 88.9 | −0.4 | Reduction By 0.5% | 89.8 | −6.7 | Reduction By 7.5% |

TABLE 2-continued

| | Overall Analysis | | | Responder Group | | |
|---|---|---|---|---|---|---|
| | $0^{th}$ Week Average Value | Inter-Group Difference of Change Amount | Change Rate | $0^{th}$ Week Average Value | Inter-Group Difference of Change Amount | Change Rate |
| Waist Circumference (cm) | 96.1 | −0.9 | Reduction By 1.0% | 95.4 | −2.1 | Reduction By 2.2% |

In the analysis of all 80 subjects, at the time of the $12^{th}$ week of ingestion, regarding change amounts (in comparison to the baseline $0^{th}$ week) of the body weight, the abdomen visceral fat area, the abdomen total fat area, the ratio of visceral fat/subcutaneous fat, and the waist circumference, test group values were lower than control group values. Among these, in the body fat percentage and the body fat amount, a significant difference between groups was detected.

Intestinal Flora Analysis and Selection Method of Similar Groups

Next, in order to investigate whether the anti-obesity action by the test food is affected by intestinal flora, through the following procedure, subjects were divided into groups with similar intestinal flora composition ratios, and a subgroup analysis was performed.

For all subjects, composition ratios of intestinal bacteria before test food intake ($0^{th}$ week), a hierarchical clustering analysis was performed by using MeV (Multiple Experiment Viewer) 4.9.0, on the basis of the Pearson's correlation coefficient. As a result, the subjects were divided into two groups with similar intestinal flora composition ratios. The hierarchical clustering, the group information associated with each subject (the intake group, and the control group), and the intestinal bacteria composition ratios at the phylum level are illustrated in FIG. 1.

A subgroup analysis was performed for two groups, and for each, evaluation items were compared between the control group and the test group. As a result, in the group 2, the anti-obesity action by the test food ingestion was remarkable. That is, in the group 2, an inter-group difference (−1.4 Kg, −1.0%) in the body fat percentage and the body fat amount was larger than an inter-group difference of the change amounts (−0.6 Kg, −0.7%) shown in the overall analysis. Also, it was found that the body weight, the visceral fat area, the total fat area, and the ratio of visceral fat/subcutaneous fat, which were not significantly different between groups in the overall analysis, were significantly reduced in the test group as compared to those in the control group (see Table 1 above). Also, as illustrated in Table 2 above, from the difference in the change rates between the overall analysis and the responder group analysis, it was clearly found that when probiotic bacteria were ingested by responders having obesity-type intestinal flora, anti-obesity effects such as more remarkable body fat reduction, visceral fat area reduction, and waist circumference reduction were obtained.

Also, in addition to the remarkable anti-obesity action in the body composition, in the group 2, the fasting blood glucose, which was not significantly different between groups in the overall analysis, was significantly improved in the test group, as compared to that in the control group (see Table 1 above). Also, regarding the improvement action of the fasting blood glucose, from the difference in the change rates between the overall analysis and the responder group analysis, it was found that when probiotic bacteria were ingested by responders having obesity-type intestinal flora, a more remarkable improvement action of the blood glucose level was obtained.

Figure 2:
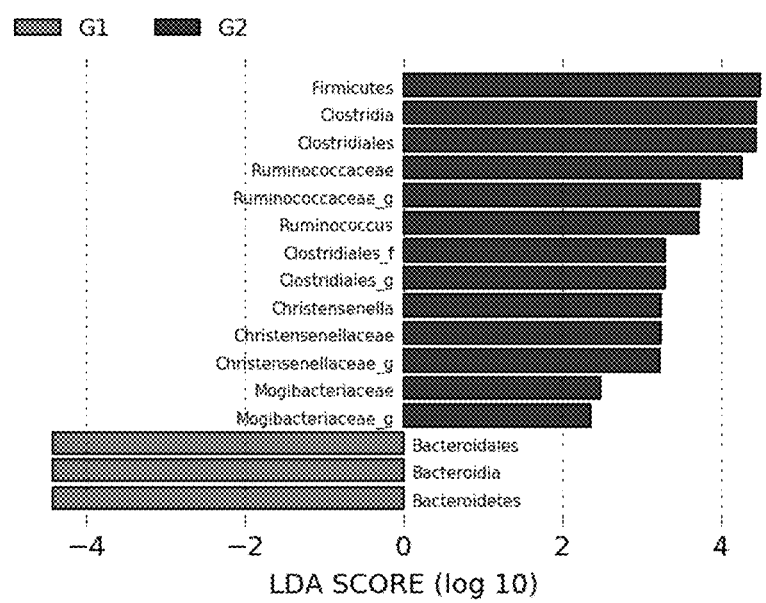
FIG. 2 illustrates analysis results by LEfSe on characteristic intestinal bacteria in groups of FIG. 1 (a group (G1) and a group 2 (G2)).

Characteristics related to an intestinal bacteria composition, which were included in the two groups classified by the degree of similarity of intestinal bacteria, were analyzed by using a LEfSe (Linear discriminant analysis Effect Size) method. As a result, as illustrated in FIG. 2, it was found that there were many phylum Firmicutes in the group 2 (the responder group) in which the anti-obesity action by the test food was remarkable, while the group 1 characteristically had many phylum Bacteroidetes. Table 3 below illustrates the basic statistics of the ratio of the phylum Firmicutes to the phylum Bacteroidetes in the group 1 and the group 2 in FIG. 1.

TABLE 3

| | Group 1 | Group 2 |
|---|---|---|
| N (Number) | 59 | 21 |
| Average Value | 0.8 | 2.6 |
| Standard Error | 0.4 | 1.2 |
| Minimum Value | 0.2 | 1.3 |
| Maximum Value | 1.7 | 6.2 |
| Medium Value | 0.7 | 2 |
| 25% Percentile | 0.4 | 1.5 |
| 75% Percentile | 1 | 2.6 |

3. Conclusion

In this Example 1, it was found that ingestion of a test food containing *Bifidobacterium breve* MCC1274 as an active ingredient reduces the body fat percentage, the body fat amount, and the waist circumference in healthy adults. Also, as a result of analyzing the relationship between an anti-obesity action and intestinal flora of a subject before intervention, it was found that the anti-obesity action by test food ingestion was remarkably high in a group having a high ratio of the phylum Firmicutes to the phylum Bacteroidetes, which is generally called obesity-type intestinal bacteria. Also, especially, it was suggested that the anti-obesity action remarkably increases when the ratio of the phylum Firmicutes to the phylum Bacteroidetes is 1.3 or more (more preferably, 1.5 or more, further preferably 1.7 or more).

Production Example 1

After ingestion in a culture medium containing a protein, an amino acid, and a sugar source, *Bifidobacterium breve* MCC1274 were cultured at 32 to 41° C. for 5 to 24 h. Then, from the culture solution, microbial cells (wet microbial cells) were collected by centrifugation. Freeze-drying was performed for 120 h by using a freeze-dryer (manufactured by Kyowa Vacuum), and the microbial cell mass after the end of the freeze-drying was physically crushed to obtain Bifidobacteria powder. The corresponding powder may contain additives and the like which are usually blended with medicines or foods.

The corresponding powder may be used as a supplement, and also, may become a drink by mixing with water. Also, by filling into a capsule container or capsule-coating, capsules for body fat reduction or capsules for waist circumference reduction may be obtained. In addition, by compression-molding, tablet confectionaries for body fat reduction or tablet confectionaries for waist circumference reduction may be obtained. By the corresponding powder, a body fat reducing effect and/or a waist circumference reducing effect may be expected.

Production Example 2

After ingestion in a culture medium containing a protein, an amino acid, and a sugar source, *Bifidobacterium breve* MCC1274 were cultured at 32 to 41° C. for 5 to 24 h. Then, from the culture solution, microbial cells (wet microbial cells) were collected by centrifugation. Freeze-drying was performed for 120 h by using a freeze-dryer (manufactured by Kyowa Vacuum), and the microbial cell mass after the end of the freeze-drying was physically crushed. The obtained Bifidobacteria powder was granulated to obtain a granular form (bacterial powder) of the corresponding bacteria. The corresponding granules may contain additives and the like which are usually blended with medicines or foods. The corresponding granules are provided daily for one week at a bacterial intake amount of $1 \times 10^8$ to $1 \times 10^{10}$ CFU/kg body weight/day.

The corresponding granules are ingested before a meal, during a meal, or after a meal. When the corresponding granules are ingested together with meals, a body fat reducing effect and/or a waist circumference reducing effect may be expected.

Production Example 3

Skim concentrated milk, cream, sucrose, and room-temperature water were mixed by using a mixer, and heated to 70° C. and dissolved. Then, after homogenization by a homogenizer at a pressure of 15 MPa, heating sterilization was performed at 90° C. for 10 min, followed by cooling to 40° C. To this, *Bifidobacterium breve* MCC1274 and a commercially available lactobacilli starter (a mixed culture of *Streptococcus thermophiles* and *Lactobacillus bulgaricus*) were added and mixed, and then 100 g was filled into a paper cup. By fermentation at 38° C., curds were formed, and then were cooled to 10° C. or less to obtain stationery-type fermented milk. The obtained fermented milk contained $1 \times 10^8$ CFU/g or more of Bifidobacteria.

When the corresponding fermented milk is ingested before a meal, during a meal, or after a meal, a body fat reducing effect and/or a waist circumference reducing effect may be expected.

INDUSTRIAL APPLICABILITY

The composition for reducing body fat and the composition for reducing waist circumference according to the present technology have an excellent body fat reducing action or a waist circumference reducing action, and thus may be used in a wide range of fields such as medicines, quasi-drugs, foods/drinks, and feeds for body fat reduction and/or waist circumference reduction.

---

The invention claimed is:

1. A method of treating an obese human subject, said method comprising:
   i) measuring ratio of bacteria of the phylum *Firmicutes* to bacteria of the phylum Bacteroidetes in the intestinal flora of a group of obese human subjects,
   ii) selecting subjects wherein said ratio is 1.3 or more; and
   iii) administering to said subjects selected in ii) a composition comprising *Bifidobacterium breve* MCC1274 (FERM BP-11175), resulting in said subjects selected in ii) to have a lower Body Mass Index ("BMI") than prior to said administering,
   wherein said composition is selected from the group consisting of a food, drink, medicine, and quasi-drug.

* * * * *

SEQUENCE LISTING

```
<160> NUMBER OF SEQ ID NOS: 4

<210> SEQ ID NO 1
<211> LENGTH: 32
<212> TYPE: DNA
<213> ORGANISM: Artificial Sequence
<220> FEATURE:
<223> OTHER INFORMATION: Tru357F Primer

<400> SEQUENCE: 1
cgctcttccg atctctgtac ggraggcagc ag                                  32

<210> SEQ ID NO 2
<211> LENGTH: 37
<212> TYPE: DNA
<213> ORGANISM: Artificial Sequence
<220> FEATURE:
<223> OTHER INFORMATION: Tru806R Primer

<400> SEQUENCE: 2
cgctcttccg atctgacgga ctachvgggt wtctaat                             37

<210> SEQ ID NO 3
<211> LENGTH: 73
<212> TYPE: DNA
<213> ORGANISM: Artificial Sequence
<220> FEATURE:
<223> OTHER INFORMATION: Bar code Primer Fwd
<220> FEATURE:
<221> NAME/KEY: misc_feature
<222> LOCATION: (30)..(37)
<223> OTHER INFORMATION: n is a, c, g, or t
```

```
-continued

<400> SEQUENCE: 3
aatgatacgg cgaccaccga gatctacacn nnnnnnnaca ctctttccct acacgacgct    60
cttccgatct ctg                                                      73

<210> SEQ ID NO 4
<211> LENGTH: 69
<212> TYPE: DNA
<213> ORGANISM: Artificial Sequence
<220> FEATURE:
<223> OTHER INFORMATION: Bar code Primer Rev
<220> FEATURE:
<221> NAME/KEY: misc_feature
<222> LOCATION: (25)..(32)
<223> OTHER INFORMATION: n is a, c, g, or t

<400> SEQUENCE: 4
caagcagaag acggcatacg agatnnnnnn nngtgactgg agttcagacg tgtgctcttc    60
cgatctgac                                                           69
```